United States Patent [19]
Lehmer et al.

[11] Patent Number: 5,491,757
[45] Date of Patent: Feb. 13, 1996

[54] FIELD TESTER GAZE TRACKING USING CONTENT ADDRESSABLE MEMORIES TO IMPROVE IMAGE DATA ANALYSIS SPEED

[75] Inventors: Donald E. Lehmer, Berkeley; Alan R. Kirschbaum, Oakland, both of Calif.

[73] Assignee: Humphrey Instruments, Inc., San Leandro, Calif.

[21] Appl. No.: 172,136

[22] Filed: Dec. 22, 1993

[51] Int. Cl.$^6$ .............................. A61B 3/024; G06K 9/78
[52] U.S. Cl. .............................. 382/128; 382/291; 348/78; 351/210
[58] Field of Search .............................. 382/6, 2, 48, 117, 382/128, 291; 351/210, 206; 348/78; 365/49

[56] References Cited

U.S. PATENT DOCUMENTS

| | | | |
|---|---|---|---|
| 1,960,111 | 5/1934 | Kirk | 351/225 |
| 4,145,123 | 3/1979 | Krahn | 351/226 |
| 4,429,961 | 2/1984 | Scheingorn | 351/226 |
| 4,748,502 | 5/1988 | Friedman et al. | 348/78 |
| 4,854,694 | 8/1989 | Hirano | 351/224 |
| 4,928,260 | 5/1990 | Chuang et al. | 365/49 |
| 4,950,069 | 8/1990 | Hutchinson | 351/210 |
| 4,973,149 | 11/1990 | Hutchinson | 351/210 |
| 5,008,946 | 4/1991 | Ando | 382/2 |
| 5,066,117 | 11/1991 | Matsumura | 351/226 |
| 5,214,456 | 5/1993 | Gersten | 351/206 |
| 5,220,361 | 6/1993 | Lehmer | 351/226 |

FOREIGN PATENT DOCUMENTS

| | | | |
|---|---|---|---|
| 14692 | 8/1993 | WIPO | 351/210 |

OTHER PUBLICATIONS

Myers, Glenn A., et al, "Eye Monitor", *IEEE Journal*, Mar. 1991, pp. 14–21.

ISCAN® Eye Movement Monitoring Research Laboratory, brochure, 1989.

*Primary Examiner*—Michael T. Razavi
*Assistant Examiner*—Larry J. Prikockis
*Attorney, Agent, or Firm*—Townsend and Townsend and Crew

[57] ABSTRACT

A field test apparatus and method is disclosed in which gradual movement of the head supporting chin cup is used to maintain a centered relation between the eye being tested and the trial lens frame holding the required prescription for optimum vision of the patient. During the test, alternating illumination is provided in the infrared between a central corneal reflection and an iris illuminating source which imparts a high contrast bright circular iris image surrounding a central dark pupil. Content addressable memories are used to delineate areas of contrast change for rapid and abbreviated microprocessor analysis of conventional RAM images. Both the corneal reflection image—which is a brightly illuminated spot on an otherwise dark background—and the pupillary image—which is a dark pupil surrounded by a brightly illuminated high contrast image of the iris are approximately located at their boundaries using content addressable memory. Thereafter, conventionally stored video data is processed at locations restricted to the high contrast boundaries. For location of the pupil center, special techniques are disclosed for examining the image's first and second derivatives to establish the pupil center within sub-pixel limits. These methods include sufficient data processing speed improvements to enable a time shared use of a microprocessor having gaze angle measurement as a peripheral event to instrument control, and data collection required in such field testing.

13 Claims, 8 Drawing Sheets

FIELD TESTER GAZE TRACKING USING CONTENT ADDRESSABLE MEMORIES TO IMPROVE IMAGE DATA ANALYSIS SPEED

This invention relates to a field analyzer for testing the optical perception of the retina of the human eye. The disclosed method and apparatus includes a moveable chin cup to maintain eye centration on any test frame utilized during the test and includes techniques for rapidly computing gaze direction, including the use of content addressable memories.

BACKGROUND OF THE INVENTION

In Lehmer et al. U.S. Pat. No. 5,220,361 issued Jun. 15, 1993 entitled Gaze Tracking for Field Analyzer, the inventors herein disclose a method and apparatus for tracking the gaze angle of the human eye during a so-called "field test."

A field analyzer is a device for surveying the sensitivity of a patient's retina. A spot of light, termed a point, is projected to a hemispherical projection screen for a short period of time. A patient viewing the hemispherical projection screen from the center of the sphere fixates along a line of sight to a fixation light source mounted on the surface of the bowl. The point of projection on the hemispherical projection screen controllably changes to positions spaced apart from the fixation light source. Preferably, the point is varied in intensity as the point moves from position to position on the hemispherical projection screen. A subjective determination is made by the patient by depressing a response button FIG. 1A item 30, if the point is seen. By positioning the point to known locations on the hemispherical projection screen and changing the brightness (in a total amount of about four decades), the sensitivity of the patient's retina is measured and mapped.

This simple concept has two basic optical problems interfacing to the patient. First, the patient must fixate on the center of the hemispheric projection screen. This fixation must be maintained when the point is presented, usually to the side of the patient's fixated line of sight, if the point is to fall on a consistent part of the retina. Secondly, the patient's vision usually must be properly corrected to focus the surface of the hemispherical projection screen onto the retina.

It will be understood focus is particularly critical when the sensitivity of the retina is measured at the threshold of the patient's vision perception; were the patient's focus not correct, targets that should be seen are not detected and give erroneous results. This is due to the fact that an unfocused spot of light appears dimmer than a focused one.

The patient's eyeglasses are almost always unsuitable for providing a focused view of the points on the hemispherical projection screen for at least three reasons. First, the frames of the patient's glasses will vary unpredictably in size and shape. They are an unknown in the areas of obscuration of vision and lens tilt angle. Moreover, it is vital that the conditions of testing be repeatable over a period of many years. This would be affected by changes in the patient's eye-wear.

Secondly, the optical prescription within the patient's glasses is almost always deficient for the particular focal distance (usually about 30 centimeters) required for the test. The glasses almost always do not correct the patient's vision to the distance from the patient's eye to the surface of the screen.

Thirdly, the viewing angle of the patient's glasses is usually deficient. For example, the glasses of the patient may contain bifocal lenses or variable lenses which change the focal distance of the patient as a function of the point position on the screen. Where testing of the field of vision of a patient is being made, such glasses give erroneous results.

Because of these limitations, vision during a field test is typically corrected by so-called trial lenses which are selected to provide vision corrected to the 30 centimeter focal distance and placed near the eye in a trial lens holder. Moreover, two lenses are usually required, one to correct spherical power and one to correct cylinder (astigmatic) power.

The correction of the patient's eyesight is accomplished by adding one or two trial lenses to the optical path, directly in front of the patient's eye. These usually round lenses are made in a variety of sphere and cylinder powers and are selected by the operator based upon the patient's prescription, corrected to 30 centimeters, the radius of the hemispherical projection screen.

The standard trial lenses are relatively small in diameter (on the order of 3.5 cm). The center of the trial lenses should be placed in the approximate center of the eye to avoid prismatic effects associated with strong lenses. Additionally, the trial lenses should be close to the eye, to prevent the obscuring of the patient's vision by the trial lens holder or lens frame. Most field testing is done within a 30 degree angle from the fixation axis. Closeness is even more important when strong positive lenses are used as they make the viewing angle through the lenses smaller by magnifying the bowl.

In all known field test devices to date, the position of the lenses is fixed relative to the center of the screen, requiring the position of the patient's eye to also be fixed. This state is monitored by a video camera FIG. 1A item V and presented to the operator as a surveillance tool. Movement of the patient's eye to re-center same in the trial lens may require adjustment of the chin cup by the operator.

Field analyzers typically use the ambient screen light for illumination of the video field. The ambient screen light of most field testers comes from the uniform illumination of the hemispherical projection screen surface, this illumination being provided to give uniform contrast to the projected points. It is also known to illuminate the eye from lights mounted on the trial lens holder using infra-red wavelengths to prevent the patient from detecting the lights.

In addition to the practical mechanical alignment problems attendant upon the use of trial lens, an additional problem exists regarding gaze direction in measuring the sensitivity of the patient's retina during the field test procedure.

Mapping the recognized variably positioned points on the spherical projection screen accurately onto corresponding positions on the retina requires that the eye does not change its angular relationship to the center of the hemispherical projection screen as the test progresses. The eye, however, is disposed in the head in such a way that changing gaze direction is easily accomplished, and in fact is the most natural thing to do when an object—such as a dim spot of light—comes into peripheral view. It therefore requires a great amount of concentration on the part of the patient to maintain a constant gaze direction. In short, the test procedure consuming normally up to 20 minutes for each eye can be very tiring on the patient.

In the normal field test the patient is asked to direct his or her vision straight ahead by "fixating" on an illuminated target. This positions the eye to image the target on the macula portion of the patient's retina, the area of the eye's highest resolution. Fixation on the center of the screen maintains a constant relationship between the points on the screen and specific locations on the retina, even with a change in the patient's head position from the central position.

It is known to check the patient's gaze direction by presenting points at the so-called optical cup or "the blind spot" of the patient's retina to be certain that such points are not seen. It is a well known natural phenomenon that overlying the optic cup on the retina of the normal eye there is an area where light is not seen. Near the beginning of a normal field test, the position of the blind spot is determined by presenting many points near the expected position of said blind spot. It is assumed that the patient is properly fixated at this time. With the position of the blind spot of the patient determined, provision is made to present points periodically to this position in the hemispherical projection screen, which position will be "blind" to the patient's eye. Normally, and assuming the patient maintains correct gaze direction, this periodically presented point is not seen and a negative response is given by the patient to the presentation of the point. A positive response indicates that the patient is not maintaining correct gaze direction at the time of presentation to the "blind spot."

It is to be understood that the presentation of points of light to the blind spot adds time to the test. Additionally, such periodic presentations constitute only a spot check of gaze direction; the patient may have incorrect gaze direction for some interval in the temporal gap between successive spot checks. At present, measuring actual gaze direction is not in common use in commercial field testers.

There are some field test instruments which measure loss of a central pupil position and claim they are measuring gaze direction. This measurement does relate to the trial lens centering issue, reporting the patient is, or is not, centered on the trial lens, but has no bearing on the actual gaze direction. It is to be understood that the eye can be gazing in virtually any angular direction with the pupil perfectly centered in the trial lens.

During field testing, it is known to observe the eye under test in a video presentation. This enables the operator to have a continuous view of the patient's eye position with respect to the trial lens holder to detect obvious deficiencies in the alignment of the patient. Unfortunately, the operator may be either periodically absent or attending to other tasks which divert his or her attention from the video presentation. Further, the operator cannot determine gaze direction from the video display and typically is unaware of when the actual point is presented, the only time when gaze direction is important. Only pupil position can be reliably measured. There is, however, a natural relationship between eye movement activity and the likelihood of satisfactory gaze direction performance. Such video presentations require a video camera and sufficient light for the video presentation to be accurately recorded.

Field analyzers are known that illuminate the hemispherical projection screen with an even field of light generated by incandescent lamps which contain some infra-red energy. Typically, the video camera used is sensitive in the infrared spectrum. This increases the contrast for patients with a dark colored iris between light reflected from the iris and the dark pupil, as all iris colors reflect about the same amount of light with infrared illumination.

However, this illumination system also reflects light from the trial lens surface. The hemispherical projection screen partly surrounds the lens. The lens is typically not anti-reflection coated. Therefore the lens glows with infrared light captured from the hemispherical projection screen. This glow from the lens reduces the pupil to iris contrast in the video image.

In our U.S. Pat. No. 5,220,361 entitled Gaze Tracking for Field Analyzer, we propose automated movement of the trial lens holder to follow the possible movements of the head of the patient during the field test. Additionally, we disclose a method of gaze tracking which includes image subtraction and comparison of the gaze by looking at the relative positions of a reflection and the center of the pupil. This application relates to improvements over these specific techniques. To avoid unnecessary duplication, our U.S. Pat. No. 5,220,361 entitled Gaze Tracking for Field Analyzer is incorporated herein by reference.

SUMMARY OF THE INVENTION

A field test apparatus and method is disclosed in which gradual movement of the head supporting chin cup is used to maintain a centered relation between the eye being tested and the trial lens frame holding the required prescription for optimum vision of the patient. During the test, alternating illumination is provided in the infrared between a central reflex on the cornea and an overall eye illuminating source, which generates a high contrast bright circular iris surrounding a central dark pupil. During the process of saving the video image in a digital form, content addressable memories are used to generate pointers to locations of specific brightness values for rapid microprocessor analysis of the video data stored in a conventional random access memory (RAM). Both the corneal reflection position—which is a brightly illuminated dot on an otherwise dark background—and the boundary between the iris and the pupil—which is a dark central pupil surrounded by a brightly illuminated iris, are approximately located using content addressable memory. Thereafter, the examination of RAM data, representing the video image in digital form, is restricted to the locations pointed to by the content addressed memories (CAM). For location of the pupil center, special techniques are disclosed for examining the first and second derivatives of the iris to pupil boundary data to establish within sub-pixel limits the location of said boundaries. These methods allow sufficient data analysis speed improvements to enable the time shared use of a microprocessor, where gaze tracking is done when other control functions required to execute the field test are inactive.

DESCRIPTION OF THE PREFERRED EMBODIMENT

Figure 1A:
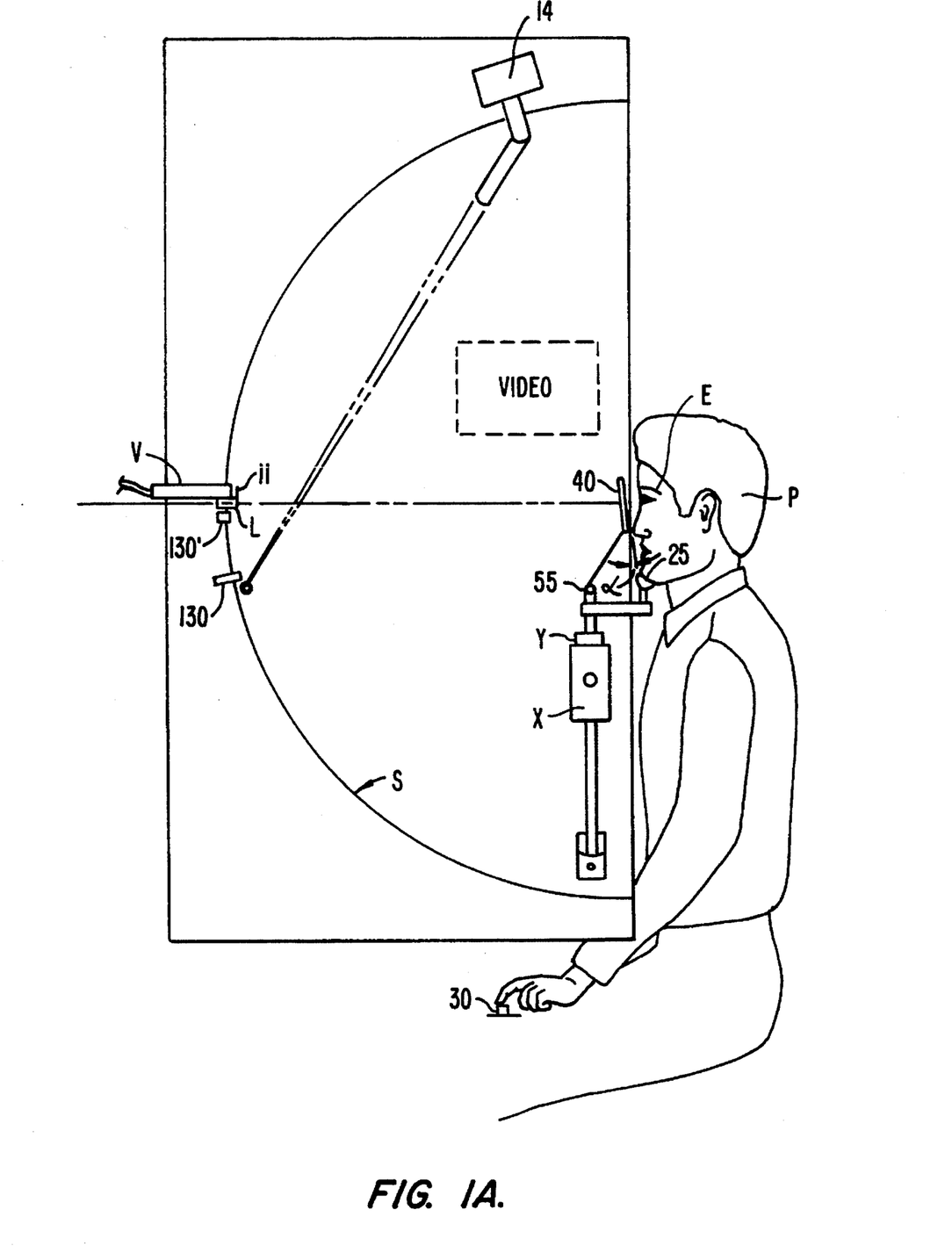
FIGS. 1A and 1B are respective side elevation and front elevation schematics of a field test apparatus incorporating the moving chin rest of this invention within the general operating environment of a field test apparatus.
Figure 1B:
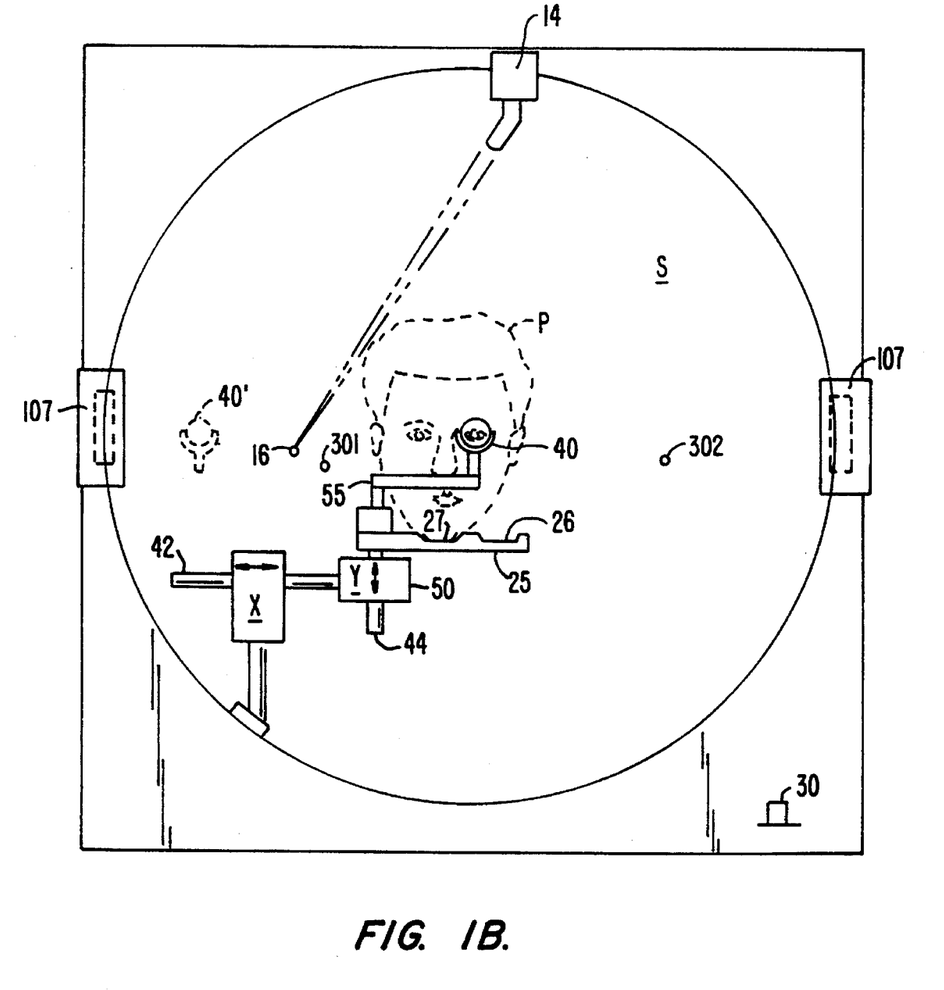

Referring to FIGS. 1A and 1B, a schematic of movable trial lens holder 40 of this invention is illustrated. A patient P is illustrated observing a hemispherical projection screen S. Patient P is here illustrated having left eye E being tested. In this test the patient P has been directed to fixate on the fixation light L at the center of the hemispheric projection screen.

Referring to FIG. 1B, the chin rest 25 illustrated has two indentations, these indentations including indentation 26 for testing the patient's right eye and indentation 27 for testing the patient's left eye. Projector 14 under the control of a computer (not shown) well known and understood in the prior art, projects spot 16 of the light on the surface of the hemispherical projection screen. The patient indicates that the spot 16 of light was seen by depressing response button 30. The response of the patient in pressing the button is recorded and mapped by apparatus well known and understood in the prior art.

The field test apparatus illustrated is old. It may be purchased from Allergan Humphrey (now Humphrey Instruments, Inc.) of San Leandro, Calif., USA under the designation Field Analyzer Series 600.

In what follows, the movement of the chin cup in incremental motion will first be discussed. This movement will be gentle persuasion to the patient to maintain his or her eye centered during the field testing procedure.

First, the method of image generation will be reviewed. Thereafter, the methods and embodiments containing the content addressable memory will be set forth. This will respectively set forth the time constraints imposed by time sharing of the processor, set forth the sequential frames and interleaved fields utilized for analysis and data collection, and illustrate arbitrary scans of eye chords with the known method of the computation of the pupil center.

Once this is set forth, the schematic analysis of data in the content addressable memory will be set forth. This will commence with the description of graphic plots of reflex and pupil data followed by illustrations of the usefulness of the first and second derivatives of the eye chord data. In the second illustration, the presence of artifact will be presumed with analysis resulting in discrimination of the artifact from valid data.

Figure 5A:
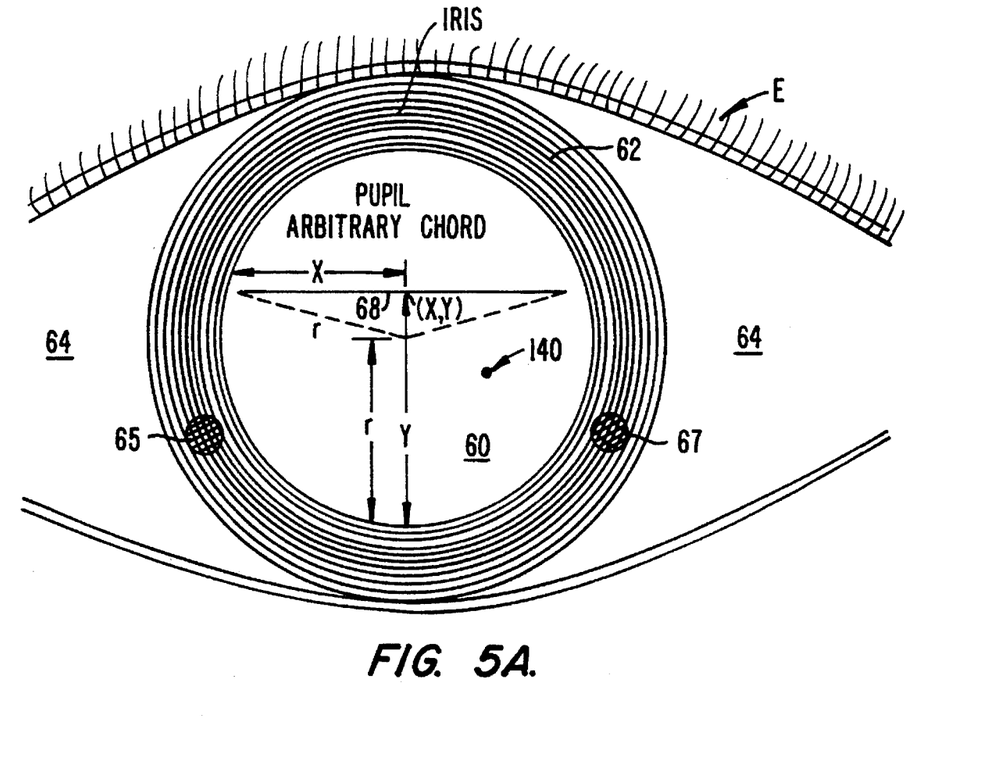
FIG. 5A is a front elevation view at the eye of the patient being field tested illustrating the measurement of an arbitrary pupil chord and normal chord bisector for locating the center of the pupil.
Figure 5B:
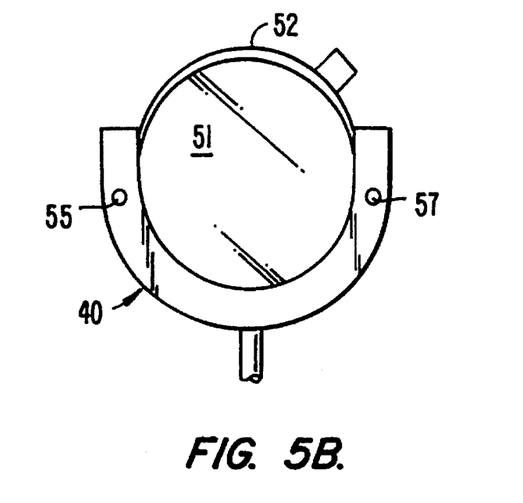
FIG. 5B is a view of the lens holder illustrating the light sources on the lens holder.

Trial lens holder 40 is shown in FIGS. 1B and 5B as a semicircular frame. Holder 40 has an active and inactive position. In the active position, trial lens holder 40 imparts optical prescription to the central 30° of vision of the patient. When the trial lens holder 40 is in the inactive position, the holder is moved out of the central position to an extreme position shown in broken lines at 40' where the trial lens holder is not in the field of view of the patient P during testing.

The reader will understand that field testers are used for two types of field test. The most frequently done field test tests the central 30 degrees from the fixation axis. The less frequent test makes measurements of visual sensitivity at viewing angles between 30 and 90 degrees from the fixation axis, to test the sensitivity of the peripheral vision. For this kind of testing, lens holder 40 is moved to the position of lens holder 40' shown in broken lines. Typically in this extended field of vision testing no trial lenses are utilized. Otherwise the points presented to extreme angles on the screen would not pass through the viewing angle of the lens. Some of the points would not be corrected by the lens and some would be obscured by the trial lens frame.

More normal field testing consists of measuring the central vision sensitivity within a 30 degree angle from the fixation axis. It will hereafter be assumed that this measurement is the measurement of interest unless specifically otherwise stated.

Chin CUD Movement

Referring to FIG. 1B, a mechanical schematic is illustrated setting forth the mechanism for the required movement of chin cup 25. The mechanical schematic shows the X motor with the body of said motor connected to the chassis of the field tester. The shaft 42 extending from the X motor contains a fine external thread. The shaft passes through the X motor which contains a mechanism such as a ball screw which is rotated by the rotor of the X motor. Since the shaft is prevented from the rotating by the mechanism, the rotation of the nut causes translation of the Y motor responsive to rotation of the X motor rotor. As the X motor rotor rotates, the shaft 42 moves the Y motor horizontally.

The Y motor is of similar design and is mounted on a horizontally sliding carriage 50 driven by the X motor. The Y motor is capable of moving the chin cup vertically via vertical shaft 44. The illustrated method of vertical movement is precisely analogous to the similar horizontal movement of the X motor.

The illustrated mechanism typically uses conventional linear stepper motors. These stepper motors allow the controlling computer system described below, to move the chin cup 25 to any position necessary in a vertical plane in front of the eye to account for the differences in physiognomy among patients.

It will be understood that movement of the chin cup is incremental with the movement being less than that required for complete correction of eye centering. This less than full motion is to provide a persuasive movement to the chin cup of which the patient is generally unaware and otherwise not distracted from the test. The chin cup correction speed is slow, adding a correction step after each point is presented and gaze measurement made, to help maintain the patient's average head (eye) position, rather than moving rapidly, as in a true correction servo.

In practice, the chin cup, and therefore the head and the eye, is moved until the corneal reflex is centered in the video window. Centering is as previous disclosed in Lehmer et al. U.S. Pat. No. 5,220,361 issued Jun. 15, 1993 entitled Gaze Tracking for Field Analyzer. Alternately, another acceptable protocol would be to center the pupil in the video window.

The amount of chin cup motion for each correcting step is to move in the direction that would place the eye in the center of the lens, but to move only a fraction of the maximum amount. This will result in small changes and not make the total correction in one large movement.

Image Illumination

Referring to FIGS. 1A, 1B, 5A and 5B, an additional object of this invention is to determine the actual gaze direction of the eye under field test. This direction is best measured by using the relative position of the center of the pupillary opening 60 and a corneal reflection 140 produced by an infrared source 130 (or 130'; see 1A) on the surface of the hemispherical projection screen S, near the center. For example, if the eye E changes gaze direction slightly, the corneal reflection 140 of source 130 will move at a different rate than the pupil 60. This is due to the fact that the cornea is a portion of a sphere, smaller in diameter than the eye, mounted on the eye. When the gaze angle is altered by the patient, the eye rotates about its center which is not the center of the spherical cornea. Hence, by determining the difference between the position of the corneal reflection 140 and the center of the pupil 60, gaze direction can be readily derived.

It will be realized, however, that all corneas are not absolutely spherical. Consequently, it is required at the beginning of the field test that an initial reading be taken and used during the test as a reference. Under controlled circumstances where it is known that the patient is properly fixated, the relationship between the center of the pupil and the corneal reflection 140 is stored as a reference. This relationship can be used during the test to determine the actual real time gaze direction. It will be understood that if the eye moves, because the patient's head moves from the center of the bowl, and the patient is still properly fixated, the measured fixation may change.

An advantage of the disclosed method for determination of the fixation of the eye is that since the absolute eye position with respect to the bowl is known by the chin cup positioning protocol, that part of the measured fixation change due solely to eye change in position may be calculated and subtracted from the measurement. This independence allows the eye to be moved away from the center of the spherical projection screen S.

Having said this much, illumination can be easily understood.

Referring to FIG. 5B, a rear elevation of the side of the lens holder 40 exposed to the patient P is illustrated. It includes two eye illuminating light sources 55 and 57. A typical trial lens 51 with frame 52 is shown within lens holder 40.

Referring to FIG. 5A, a front elevation of the eye E of patient P is shown. Reflections 65 and 67 are created by light sources 55 and 57. More importantly, it will be understood that since sources 55 and 57 are off center with respect to video camera V, a so-called dark pupil illumination of the eye will result. This dark pupil illumination will brightly illuminate the iris while leaving the pupil dark. The corneal reflection 140 is generated either by infrared light source 130 or preferably 130'. (See FIGS. 1A and 1B).

Returning to FIG. 3, it will be seen from the timing diagram there present that corneal reflection illumination occurs first and the pupil illumination occurs second. Specifically, and during Frame 1, illumination of the eye in the infrared is supplied only by light sources 130 or 130'. During Frame 2 illumination of the pupil occurs from light sources 55 and 57 on lens holder 40. Thus lighting of either the corneal reflection or the pupil in the case of this improvement is in the alternative—lighting of both the corneal reflection and the pupil simultaneously is not used.

Having set forth the scanning utilized with this invention, the subject of the time constraints required by time shared use of a microprocessor can be understood.

Time Constraints

Figure 2:
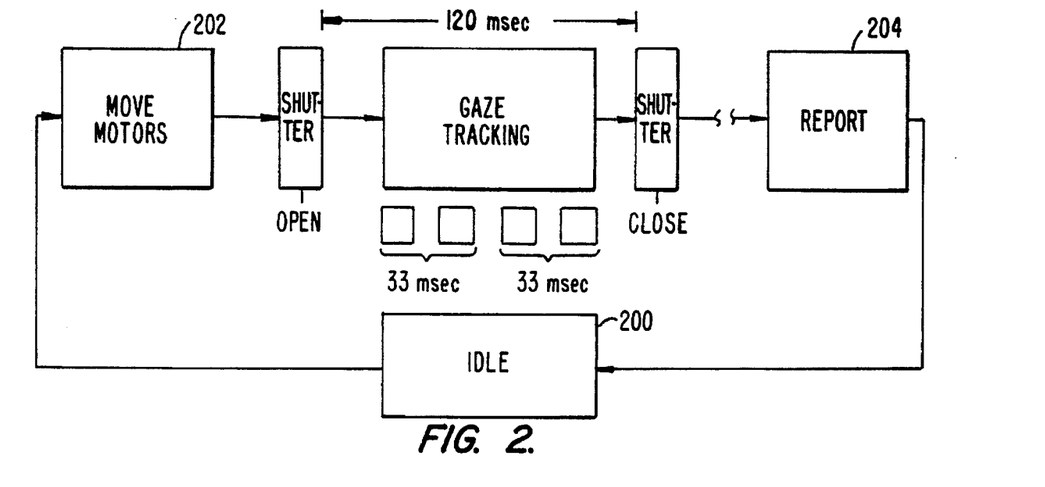
FIG. 2 is a block diagram illustrating a typical required time sharing cycle or loop for the gaze tracking function of this invention specifically illustrating the narrow time window available for the automated observation of gaze tracking information.

Referring to FIG. 2, a typical time sharing loop is shown. In the case that the processor is not idle, as at 200; said processor is involved with moving motors for the adjustment of chin cup 27 or generation of an additional spot 16 (see FIGS. 1A and 1B); or reporting data; else the processor will be in a gaze tracking mode. This gaze tracking mode will require that the image with the corneal reflection of light source 130 be compared to the image with a dark pupil (See FIG. 5A).

Returning to FIG. 3, two separate video frames (Frames 1 and 2) are required to make this comparison. The window XX located in the approximate center of the image represents the area covered by the video memory used in gaze tracking. The first Frame 1, has two fields (1 and 2) containing video data created when the corneal reflection illumination was present. This bright dot of light will appear on the cornea approximately centered in the video frame clear of lens holder 40 as illustrated at Frame 1, Field 1. It will be noted that the lens holder 40 is indicated in broken lines; it will not appear in the gaze tracking data since it is outside of the window XX.

Figure 3:
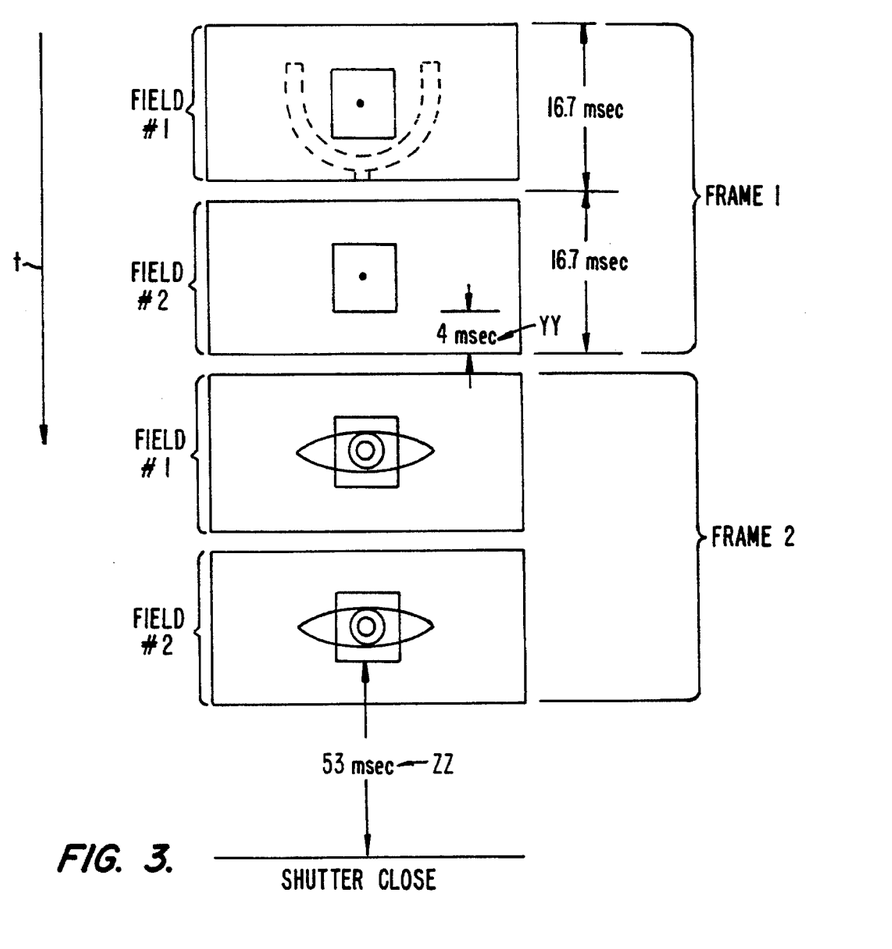
FIG. 3 is a representation of two video frames with each frame consisting of two interleaved fields, this diagram being useful for understanding the gathering of the raw data and the time available for the time shared gaze tracking computation.

Frame 2 also has two fields containing video data created when the pupil illumination was present, the bright iris with a dark pupil of eye E.

In both frames, it will be observed that the corneal reflection and eye E only occupy a small portion of the video field. The image of the pupil is maintained at this small size to offer the operator a larger field of view on the operator's control panel to aid in the initial alignment of the patient.

It further allows the size of the video memory to be reduced for gaze tracking, active in the window XX covering a small area inside the trial lens. This excludes the trial lens holder from the video data.

Another advantage of the small window is that it can be converted to a digital form in about one fourth of the available time of the camera field, allowing the time remaining for computation. Given the fact that there is only one video memory, the computation of the corneal reflex must be done in the time between the end of the window and the beginning of the next field, at which time the corneal reflex data may be over-written by the dark pupil data. It is for this reason that the content addressable memory protocol of this invention has been developed.

With reference to FIG. 3, it will be understood that the video RAM (Random Access Memory) used to store an image of the eye for gaze measurement, contains a digital image, organized as an array. In practice the RAM dimensions are 128 dots by 128 lines (16k). The data is stored only in a small window, positioned inside the trial lens. There is a byte for each pixel, where the value of the byte represents the brightness value of the pixel.

There are two pattern recognition requirements, the finding of the cornea reflection, and the finding of the pupil edges. The former requires the centroid of a bright event to be found and the later requires the edges of a dark area to be found on each video line.

The corneal reflection and the pupil edges are found using two consecutive video frames, one frame with just the reflection from the cornea (see above) and one frame with an illuminated iris and a dark pupil and no central corneal reflections.

Scan and Memory Loading

Having reviewed the video frames taken by video camera V, attention can now be directed to the loading of video data into the respective content addressable memories. This can be understood with reference to the schematic of FIG. 4. The block diagram contains four random access memories (RAMs), 500–503. RAMs 500 and 501 can store the video data in a conventional manner.

Figure 4:
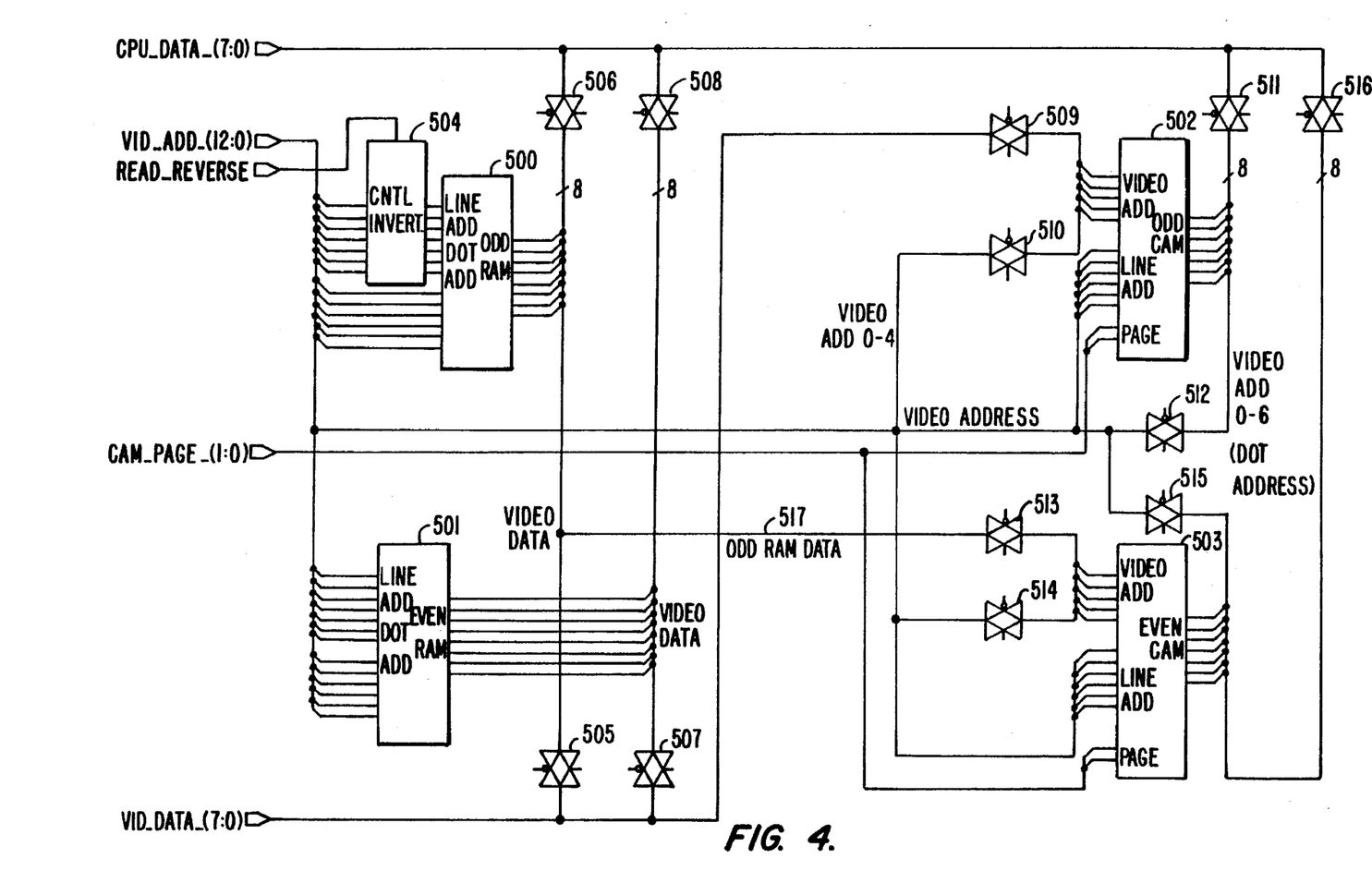
FIG. 4 is a video memory block diagram illustrating the interconnection required to form a memory system for sorting a digital representation of the video data in RAM and also in content addressable memories.

The address VID_ADD_(12:0) is generated by addressing logic (not shown) which has two modes, a sequential address, changing at high speed, to capture the video image, or an address connected to the microprocessor address system, to read the resultant stored data.

The address is shown as two sets, the dot address (7 bits for 128 dots) and the line address (6 bits for 64 lines). The function of item 504 is to complement the dot address when READ_REVERSE is true, to make the dot address appear to reverse, allowing RAM 500 to be read back in reverse, as required to find the left hand edge.

The data to/from RAM 500 can be selected either from VID_DATA_(7:0), the digital representation of the video data, via switch 505, or from the microprocessor data port via switch 506. The former is used to save the video image and the later is used to read the resultant data in the RAM.

RAM 501 is similar, using switches 507 and 508. In practice, RAM 500 saves the first video field and RAM 501 saves the second field. The corneal reflection data must be processed between frames, during time period YY, since the RAMs are filled with pupil data on the next two fields. The time to process the pupil data before the shutter closes is ZZ.

RAM 502 is used as a CAM when loading video data and as a RAM when the resultant data is to be reviewed by the microprocessor. In the CAM mode, switch 509 and 512 are closed, allowing the five least order address bits to be controlled by the five high order video data bits. This causes the CAM to have 32 bins. The six higher order address bits are connected to the line address, making an array of video intensity level, the horizontal axis, by video line, the vertical axis.

Switch 512 places the 7 bit dot address onto the data input such that the CAM cell will contain the dot number valid at the time the cell is addressed and written.

To review the data, switches 510 and 511 are closed, the former completes the RAM address structure, and the later places the RAM data on the microprocessor data port.

RAM 503 is similar to RAM 502 above, except the video data input is connected directly to the data output from RAM 500, via path 517. This path is used while RAM 500 is being read backwards during the second pupil field, to find the left edge. For CAM operation, switches 513 and 515 are closed. For RAM operation, switches 514 and 516 are closed.

To allow the CAM memories to be cleared prior to use and not require same to be cleared between video fields, each CAM contain four pages, or sections, selected by the control line CAM_PAGE_(1:0). This allows a cleared CAM to be selected between fields, the first storing the corneal reflection data, and the second storing the pupil edge data. In practice only two of the four pages are used.

Content Addressable Memory Data

In the application to gaze measurement, a content addressable memory (CAM) is a RAM memory which has been organized as an array of brightness values versus line number. Thus the data in the CAM cell is the dot number in force when the cell was written. This much can be seen in FIGS. 6 and 7.

The dimensions of each CAM are 32 brightness bins by 64 lines. There are only 64 lines since it is storing data from each video field in an interlaced video environment. The data is from every other line, as compared to the data in video RAM.

The brightness bin is formed by addressing CAM with only the five highest order brightness data bits, thereby grouping the data into bins of eight, since the low order three bits in the byte are not used. Bin zero contains data from zero to seven, bin one from eight to fifteen, etc., up to bin 31 from 248 to 255 inclusive. This much can be seen on the graphic plots of FIGS. 6 and 7.

Finding the Corneal Reflection

Figure 6:
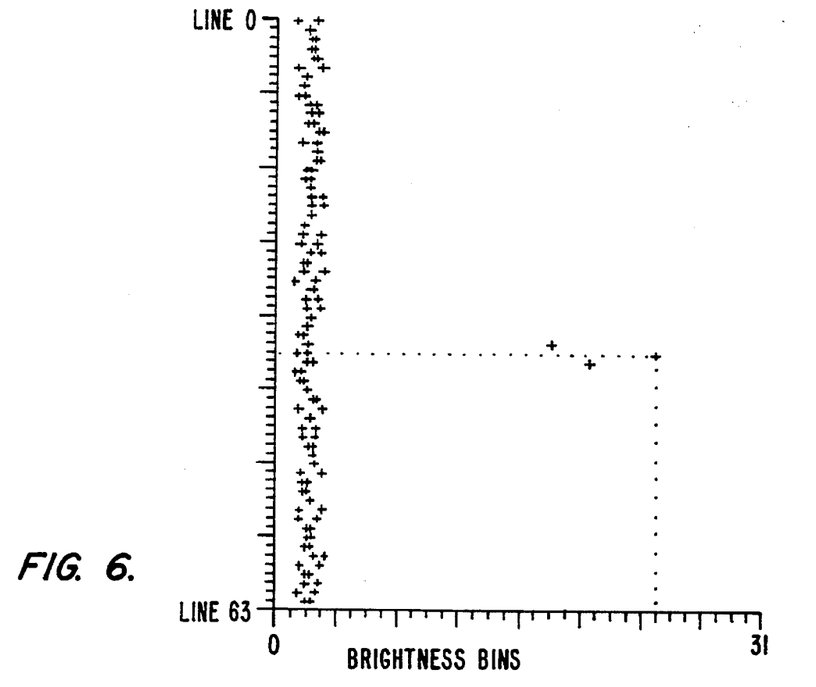
FIG. 6 is a representation of data within a content addressable memory after the presentation of the video data of a corneal reflection.
Figure 7:
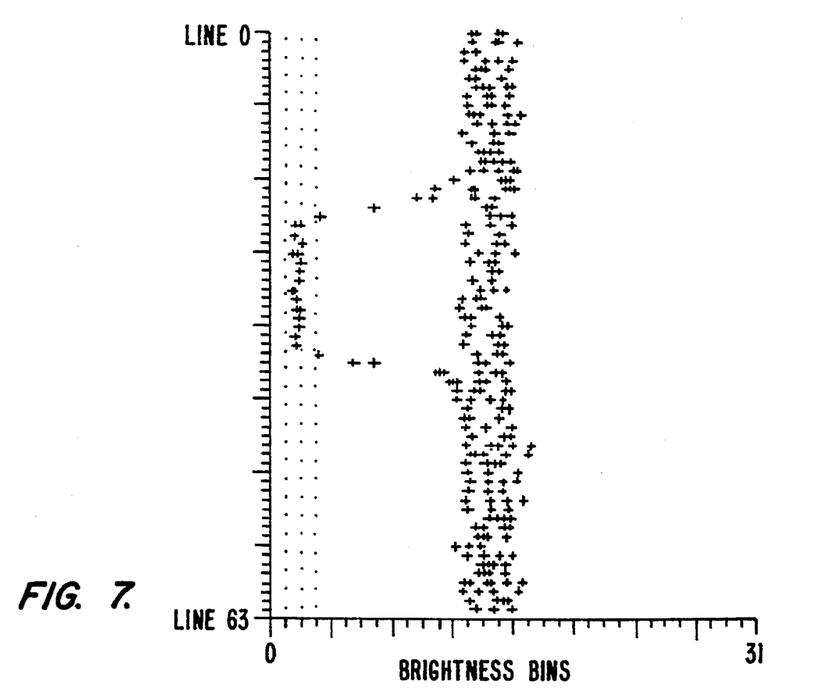
FIG. 7 is a representation of data within a content addressable memory after the presentation of the video data of a dark pupil surrounded by an illuminated iris.

FIGS. 6 and 7 are graphical representations of the pattern recognition tasks for gaze measurement, the finding of the corneal reflection and the finding of the pupil edges. It depicts CAM memory as an array, video Line 0 at the top and video Line 63 at the bottom. The horizontal axis represents the 32 video amplitude bins, where bin 0 has the range of 0 to 7, bin 1 has the range of 8 to 15, etc., until bin 31 has the range of 248 to 255 inclusive.

White space in the graphical presentation indicates that the CAM cell contains a zero, the initial value in the CAM array. A plus sign indicates that the cell contains some non-zero data, the dot number in RAM that was in force when the CAM cell was last written.

If the same brightness occurred on a line more than once, typical of the pupil, the same CAM cell is written more than once, with the dot number in force at that time. In this way the dot number of the last occurrence of the brightness is saved, pointing to the right edge of the pupil, since the video camera scans from left to right.

In the case of finding the reflection from the cornea, done in the first frame of camera data, CAM can be quickly searched line by line starting at the highest bin, level 31, and continuing the line by line search at reduced bin levels until non-zero data is found. The CAM data is shown in FIG. 6. Since CAM is cleared prior to use, any non-zero data in a CAM cell indicates that the brightness level did occur on that line.

The first non-zero data in CAM points to the dot address in RAM and the line address in RAM is the same as the line address in CAM, taking into account the fact that the CAM line number is not interlaced. A pointer is thereby formed to the location of the corneal reflection data in RAM.

If the CAM is searched from bin level 31 through level 16 (if not at least half scale, it is not a bright reflection), the search will take 64 times 16, or 1K tests for non-zero data. Since the reflex LED is adjusted prior to the field test to produce a reflex near maximum brightness, the search is much shorter than the 1K worst case.

If the video RAM data were searched, with no prior knowledge, 16K bytes would have to be tested for value and compared to the running maximum. A pointer to said maximum would be retained as a pointer to search RAM for the reflex data. Prior knowledge is not available since the shutter opens about once a second and the patient could move a significant amount in that time.

Searching CAM for the first occurrence of non-zero data is a much faster task for the computer compared to evaluating the magnitude of the video data. CAM makes a significant speed increase possible.

The data stored in a CAM cell is the dot number in RAM (0–127) for the last occurrence of the brightness data in the brightness bin on a specific line. Since the data from the video camera is scanned from left to right, the data in the CAM cell is the dot address of the right edge of the video pattern.

The CAM is written at the same time as the RAM video data is stored, pointing to the location of the data in RAM.

Finding the Corneal Reflection

In the case of finding the location of the corneal reflection, done in the first frame of camera data, CAM can be quickly searched line by line starting at the highest bin, level 31. Since CAM is cleared prior to use, any non-zero data in a CAM cell indicates that the brightness level did occur on that line.

The first non-zero data is the dot address in RAM and the line address in RAM is the same as the line address in CAM. A pointer is thereby formed to the location of the corneal reflection data in RAM.

FIG. 6 shows the contents of CAM, initially cleared, when the video amplitude in the field is mostly low in amplitude, except for some lines which contain bright data. This is characteristic of the dark frame generated with only the corneal reflection generator LED on.

From this presentation it can be seen that these bright lines can be discovered by scanning down from Line 0 to Line 63 starting with the brightest bin, and continuing until a non-zero datum is found. The line number in CAM is the same as the line number in RAM since the two were saved at the same time. The contents of CAM is equal to the dot number in RAM when the datum point was saved in CAM.

Reading the contents of CAM therefore forms the horizontal (dot) pointer for RAM. In the case shown there was only one pixel with the highest brightness. The other two pixels of less brightness were not found since the search stopped when the first was found.

Note that the low level data, the eye at low illumination since the illuminators in the trial lens, or on the bowl, are off, can write into more than one bin per line. This indicates that the image has a brightness range which spans more than one CAM bin.

Finding the Pupil Edges

FIG. 7 shows the contents of CAM, initially cleared, when the video amplitude in the field is mostly mid range, but also contains some dark data, characteristic of an image of the eye with an illuminated iris, the mid range data, and a dark pupil.

From this presentation it can be seen that the lines which contain the dark pupil data can be found by searching bin 1. Starting at Line 0 and searching down, the first line with non-zero datum is a line with dark data present. The location of the right edge of said data in RAM can be found by forming a pointer using the value in CAM.

To find the left edge of the pupil, the RAM data stored during Frame 2, Field 1 is read backwards into another CAM forming a similar CAM image. This occurs since reading the RAM data backwards is equivalent to a camera that scans right to left, making the last occurrence of a specific video level occur on the left edge. With both of these CAMs available the left and right edges of the pupil can be found on each line. This allows software to locate the pupil edge data in RAM and proceed to find the zero crossing of the second derivative of the video data.

Note that the video data may change so rapidly when the transition from the iris to the pupil occurs that it passes through a bin without being clocked. For this reason the CAM system works best if the lowest bin levels are used. It is likely that the flat bottom pupil will indicate the transition from pupil to iris since the pupil data does not change rapidly near the pupil level.

In practice the CAM level for finding the pupil edges is chosen by searching the lines, starting at the lowest bin level, and moving up bin levels until a non-zero datum is found. This bin and the bin above same are used in conjunction to find the edges. The bin with datum which indicates a larger pupil is used. This allows the pupil data to split a level, some of the data in one level, and some of the data above that level, without error.

Note that the pupil falls into just a few bins since it is dark. The iris falls into many bins since it has many brightness levels.

It should be obvious why the trial lens holder cannot be included in the video window. It would appear dark, and would be the last occurrence of said dark data, writing over the pupil data. It is important that the pupil be the only dark data in the video window XX.

It should also be obvious that reflections from the trial lens of the bowl, such as fingerprints, would cause changes in the dark pupil data and confuse CAM. This is why the bowl is illuminated in non-infrared light and the camera is restricted to the infra-red spectrum. Reflections from the trial lens due to bowl illumination are not visible to the camera.

In the case of finding the location of the dark pupil area on each line, CAM can be searched at a low bin level to find the dark pupil area. The pointer in CAM will point to the edge of the pupil opening where the brightness increases when the iris occurs and the brightness data no longer falls into the pupil brightness bin. The last value written into the CAM cell forms a pointer to RAM were the edge of the pupil can be found on that line.

The video data is interlaced, that is, half of the image (field) is sent, scanned left to right, followed by the interlaced field (one half line down), to form a complete image (frame). This is part of the standard television transmission method.

As previously set forth with respect to FIG. 4, in hardware, the data from one frame is stored in two video RAMS, one for each field, and two CAMS. During the first field the video data is stored in the first RAM and CAM. In the case of finding the pupil, the CAM contains pointers to the right edge of the pupil.

During the second field, the video data is stored in the second RAM and the first RAM data is read backwards into the second CAM. As a result, the first field is used to find the right and left edges of the pupil, since reading the RAM data backwards causes the last occurrence of a specific brightness bin to occur on the left edge of the pupil.

After this operation, RAM contains an interlaced image of the dark pupil ready for detailed examination and the CAMs contain pointers to both the left and right pupil edges. In practice, a constant is added to the right pointer and subtracted from the left pointer to form starting points for the determination of the zero crossing of the second derivative, as outlined in the original disclosure.

In practice the CAM level used to find the dark pupil is determined by searching one of the CAMS, line by line, from bin 0 to bin 7, to find the first non-zero cell. The level with the first CAM data is the proper bin to use (a flat bottom is assumed). The bin selected and the bin above same are used in conjunction to find the left and right pointers to the pupil edges for each line.

Finding the Corneal Reflection Centroid

As outlined above, a pointer is found to the location in RAM of the corneal reflection. In practice a small box is centered around the pointer, expected to contain all of the corneal reflection data. In practice the box is 16 pixels by 16 lines. Such data is spread over more than one pixel, especially if the video camera is not perfectly focused or the corneal reflection is very bright.

The data in the box, over a half amplitude threshold, is added together to form an amplitude sum. The data is also multiplied by the dot number and the line number and each product totalized. The resultant three sums are used for the determination of the centroid.

The centroid is determined by dividing each of the product sums by the amplitude sum to form two results, the sub-pixel dot and line location of the corneal reflection centroid. This method is termed "the weighted average method".

The procedure is as follows:

Amplitude Sum—Σ videodata (inside box and above threshold)

Dot Sum—Σ (Video Data)*(Dot #)

Line Sum—Σ (video data), (Line #)

Sub pixel dot #—Dot Sum/Amplitude Sum

Sub pixel line #—Line Sum/Amplitude Sum

The use of CAM allows the entire process, both gathering of the video data and analysis of said data, to be accomplished during the time the shutter is open, the time when the point is presented to the patient. This allows a cost reduction as compared to a higher speed computer without CAM, or a separate computer to analyze the data after the shutter is closed.

Using the First Derivative as a Pointer to the Second Derivative

Lehmer et al. U.S. Pat. No. 5,220,361 issued Jun. 15, 1993 entitled Gaze Tracking for Field Analyzer outlines the use of the zero crossing of the second derivative as a method of finding the amplitude midpoint of the pupil to iris transition independent of the video amplitude.

In practice, the process of taking the derivative increases the sensitivity to noise in the video data, in particular where the transition is not smooth. To find the zero crossing of the second derivative, the maximum value of the first derivative is found and used to limit the search for the zero crossing of the second derivative. See FIGS. 8 and 9.

This method restricts the second derivative zero crossing search to exclude unwanted data caused by noise. The first derivative is less sensitive to noise than the second. An example of this exclusion can be found in FIG. 9, where noise 300, a premature dark area prior to the pupil (such as an eyelash covering the iris) is rejected since the maximum of the first derivative occurs at 301, the edge of the pupil. This restricts the second derivative zero crossing detection activity to a small area surrounding 301. The bright spot in the pupil opening, item 303, a corneal reflection from an unknown source was also rejected.

Using Two CAM Bins to Find Pupil Edges

The use of CAM to find the edge of the pupil by examining the lower bins, where the dark pupil data is expected to be found, is simple in the ideal case. In practice, the selection of the number of bins used is crucial. The goal is to find the left and right edges of the pupil in a simple manner using CAM. If the CAM process is too complicated to analyze, it loses its time saving features.

Figure 8:
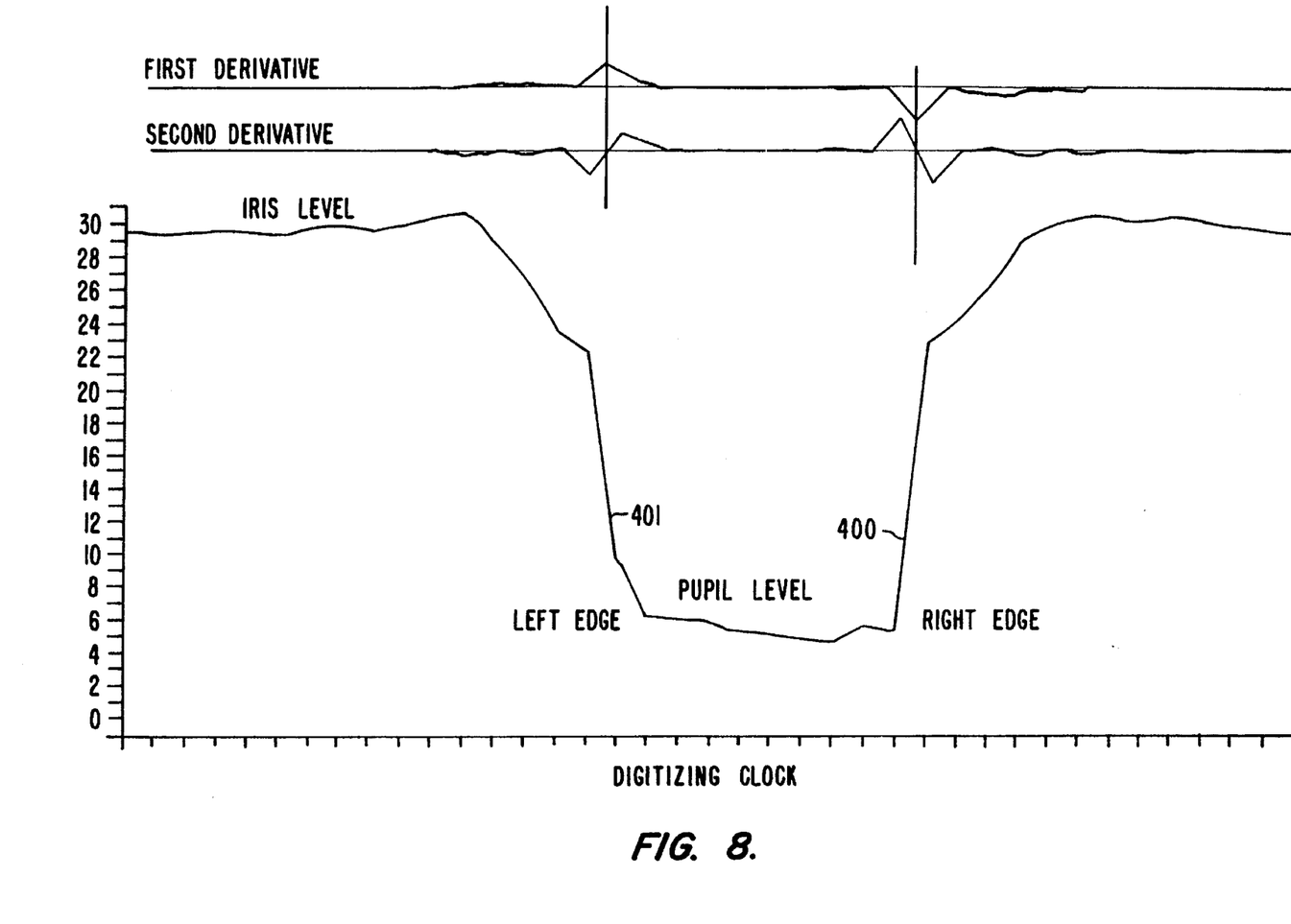
FIG. 8 is a composite diagram representing the video data from a single horizontal video scan line corresponding to the arbitrary chord according to FIG. 5. The image data with the first and second derivative of the image data is presented; and, FIG. 9 is a composite diagram representing the video data from a single horizontal video scan line corresponding to the arbitrary chord according to FIG. 5, said image containing deliberate artifacts common to image processing. The image data with the first and second derivative of the image data is presented.

To visualize the problem, and with reference to FIG. 8, the dark pupil on one video line can be considered as an inverted truncated triangle suspended from the brightness level of the iris. As illustrated in FIG. 8, the CAM levels form horizontal lines intersecting the triangle at specific fixed levels and the data in each of the 32 CAM cells is the horizontal position on that line of the intersection with the video data.

Vertical lines also exist, the time at which the video data is sampled by the digital frame grabber hardware and stored in CAM. The data saved in a specific CAM cell occurs at the intersection of a vertical clock line and the video data. For example, consider CAM level 12 (FIG. 8) which intersects the data twice. In theory, the horizontal position would be written into CAM cell 12 twice, the final value being the last written value, position 400 for a left to right scan, or position 401 for a right to left scan.

In practice, the slope of the triangle's edge can be abrupt. If the number of bins is large, the horizontal lines are close together, the pupil edge may fail to write into a specific bin since that particular level was not sampled. The bottom of the pupil may cause many CAM levels to be written. This would require a later test to find the level which contained a dot number nearest the edge.

If the number of bins is small, it becomes more difficult to separate the iris from the pupil. More careful control of camera gain and illumination would be necessary to assure that the iris and the pupil are in separate bins.

To further complicate matters, the brightness value of the pupil can have many values during the video sweep due to noise and may be placed in two bins. This sharing is caused by forcing the data into digital bins, and the amount of sharing is data dependent.

CAM Search Method

The method used for finding the CAM bin of interest is to search the video lines at the lowest bin level and increment the bin level and continue the search. The first non-zero data indicates that pupil brightness data occurred on that line. This may be a single point where the pupil dipped down into the CAM level and the level may not contain the left and right edges. To get the pupil edges, the CAM level determined above is combined with the next higher level.

This evaluates two CAM bins but allows one CAM bin resolution. This is superior to having only half as many bins. If non-zero data is in both CAM levels, the method of data evaluation selects the data from the CAM level which forms the largest pupil opening. The left most data is used for the left edge and the right most data is used for the right edge.

Finding the First Derivative

FIG. 8 illustrates a single video line crossing the pupil. The bright video value near the top of the page represents the iris and the dark video value near the bottom of the page represents the pupil. Also shown is the first and second derivatives of the data. These may be easily obtained utilizing standard software techniques.

Regarding the obtaining of the first derivative, it has been found advantageous to use the data from every other video dot for finding the pupil edge, or every other video line for finding the pupil bottom to develop the derivative information. For example, utilizing data from video dot or line 0 and 2, 1 and 3, 2 and 4 produces a more pronounced derivative with freedom from noise.

Summary

The data is clocked into digital memory at each of the vertical lines (FIG. 8 and 9), and the brightness at that time is stored in RAM and is used to select the CAM bin. If the data falls into a specific CAM bin, the dot number (horizontal position) is written into that CAM bin.

Figure 9:
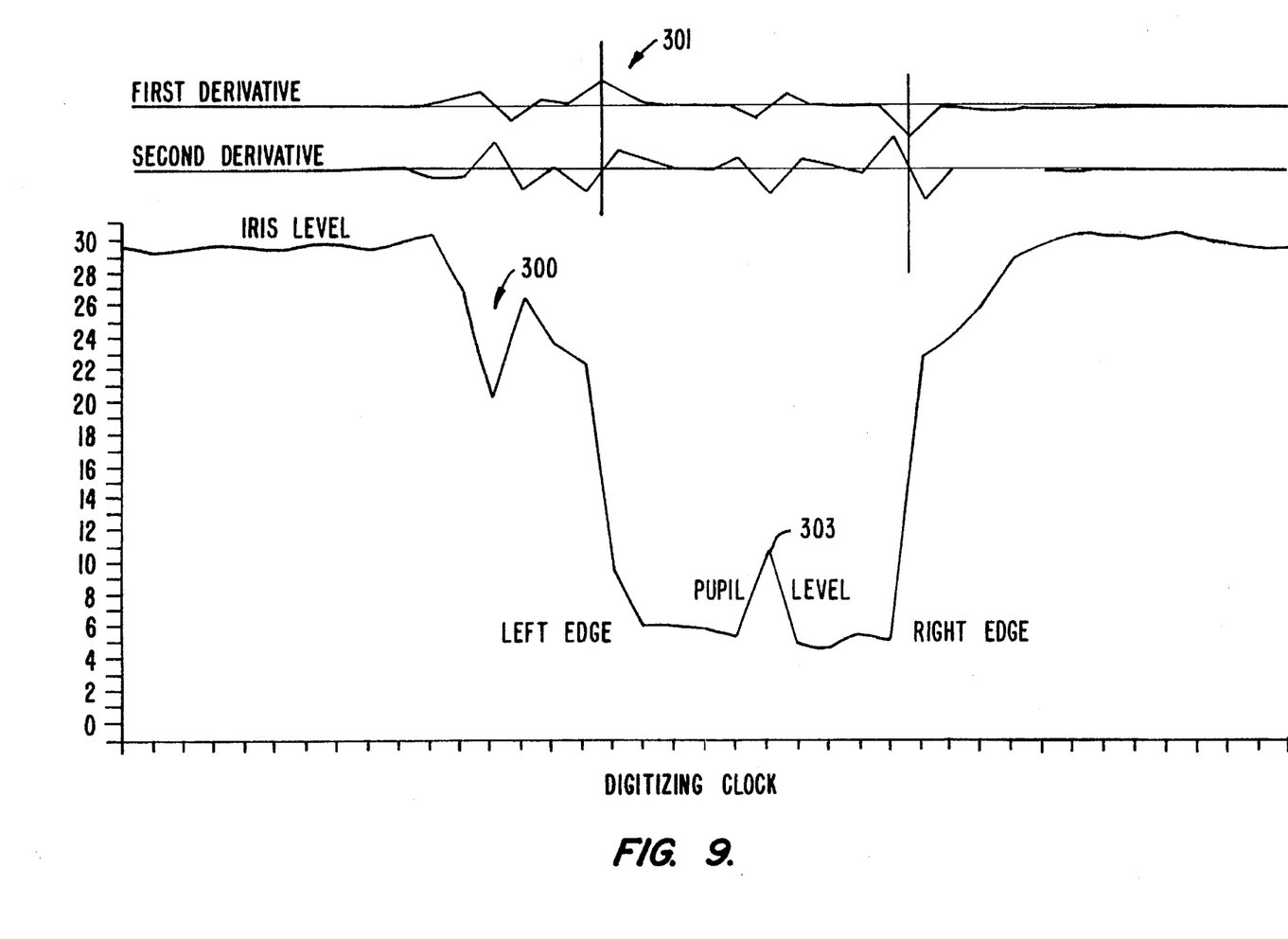

The last occurrence of data that fits in the bin will be retained in CAM and points to the right edge, if the data is being scanned into memory from left to right. When the RAM data is read backwards into CAM, the left edge is retained.

Note that the first derivative has a single peak and the second derivative changes sign at the horizontal position of maximum vertical slope. This is selected as best horizontal position for measuring the pupil edges.

Note further that the slow changes in brightness before the pupil are not detected by this method.

Note that the dark pupil data falls into two CAM levels and that searching the first lowest level with non-zero data does not return accurate edge positions.

Note that the rate of change of the pupil to iris transition is sufficiently fast that most of the CAM levels are not clocked. This is why it is desirable to search the lowest levels.

FIG. 9 is similar to FIG. 8 except a spurious disturbance has been introduced in the iris and the pupil. If the maximum of the first derivative is used to point to the search area for the second derivative, the pupil edge is found instead of the spurious data. If the search area for the second derivative covers only a small number of pixels, the spurious data is not detectable when searching for the zero crossing of the second derivative.

Such a spurious signal in the iris occurs in practice, caused by a dark speck in the iris, or an eyelash. The spurious signal in the pupil area is caused by a unwanted reflection from the cornea. In both cases the spurious signal would be rejected since the first derivative of the data is smaller than that created by the pupil to iris transition.

Referring to FIG. 5A, the next step in the process is to bisect chord 68 and starting at said bisect scan down the RAM data to find the transition from the dark pupil to the lighted iris area at the bottom of the pupil 60. This generates the vertical distance (y).

Finding of the vertical distance (y) is precisely analogous to finding one of the edges of the scans of FIGS. 8 and 9. To avoid repetition, such a procedure will not be further described here.

The horizontal distance (x) is the length of the chord from the bisect to one end of the chord 68.

The calculation is based on the Pythagorean theorem. As is well known, the sum of the squares of the two sides of a right triangle equals the square of the hypotenuse. The triangle is shown in FIG. 5A formed by half of the chord 68, the difference between the vertical component and the unknown radius (y-r), and the unknown radius (r) as the hypotenuse. This is only true if the pupil is a true circle, an assumption for this measurement. The mathematical method applies equally well to an arbitrary chord 68 placed below the pupil 60 center.

The formulation for this is as follows:

By the Pythagorean Theorem:
$a^2 + b^2 = c^2$
$(y - r)^2 + x^2 = r^2$
$y^2 + r^2 - 2yr + x^2 = r^2$
$2yr = x^2 + y^2$
$r = (x^2 + y^2) \div (2y)$
Center = $Xo, Yo - (y - r)$ Where
r=unknown radius
x=half of the chord length
y=distance from chord to bottom of pupil and Xo,Yo= location of arbitrary chord bisect.

While the above algebraic form may appear to be complex, this is a rapid and easy calculation for a computer.

What is claimed is:

1. A method of processing a video image having first and second fields of image intensity data with known boundaries of high contrast comprising the steps of:

providing first and second read and write memories each addressable by row number and column number addresses for storing image intensity data of the first and second fields of the video image at the row number and column number addresses;

providing first and second content addressable memories addressed by row number address and an address related to image intensity for storing the column number addresses of the first and second fields of the video image at the row address and the address related to image intensity;

initially clearing the first and second content addressable memories;

loading the first read and write memory with row number address and column number address to store image intensity data from the first field of the video image;

loading the first content addressable memory by row number address and an address related to image intensity to store column number address from the first field of the video image;

loading the second read and write memory with row number address and column number address to store video intensity data from the second field of the video image;

loading the second content addressable memory by the row number address and an address related to image intensity to store column number address from the first read and write memory reading the data from the first read and write memory in the reverse address order with respect to the first content addressable memory;

searching the row number addresses sequentially of the first content addressable memory at a predetermined intensity level for a non-cleared content to locate a column number address;

using the column number address contained in the first content addressable memory and the associated row number address to address the first read and write memory at a location near the left edge of a high contrast boundary;

searching the row number addresses sequentially of the second content addressable memory at a predetermined intensity level for a non-cleared content to locate a column number address;

using the column number address contained in the second content addressable memory and the associated row number address to address the second read and write memory at a location near the left edge of a high contrast boundary;

providing a search protocol for searching less than all of the video image in the first and second read and write memories; and, using the search protocol to search the first and second read and write memories utilizing the row and column addresses of the predetermined intensity level whereby less than all of the video image in the first and second read and write memories is searched by the search protocol.

2. A method of processing a video image having known boundaries of high contrast according to claim 1:

wherein said predetermined level of intensity is the highest level of intensity in said video image.

3. A method of processing a video image having known boundaries of high contrast according to claim 1 and wherein:

said predetermined level of intensity is the lowest level of intensity in said video image.

4. A method of processing a video image having known boundaries of high contrast according to claim 1:

wherein said boundaries belong to a point like region.

5. A method of processing a video image having known boundaries of high contrast according to claim 1:

wherein said boundaries belong to a circular region.

6. A method of processing a video image including the iris of the human eye having first and second fields of image intensity data with known boundaries of high contrast comprising the steps of:

providing first and second read and write memories each addressable by row number and column number addresses for storing image intensity data of the first and second fields of the video image including the iris of the human eye at the row number and column number addresses;

providing first and second content addressable memories addressed by row number address and address related to image intensity for storing the column number address of the first and second fields of the video image including the iris of the human eye at the row address and address related to image intensity;

initially clearing the first and second content addressable memories;

loading the first read and write memory with row number address and column number address to store image intensity data from the first field of the video image including the iris of the human eye;

loading the first content addressable memory by row number address and image intensity data address to store column number address from the first field of the video image including the iris of the human eye;

loading the second read and write memory with row number address and column number address to store video intensity data from the second field of the video image including the iris of the human eye;

loading the second content addressable memory by the row number address and an address related to image intensity to store column number address from the first read and write memory reading the data from the memory in the reverse address order with respect to the first content addressable memory;

searching the row number addresses sequentially of the first content addressable memory at a predetermined intensity level for a non-cleared content to locate a column number address;

using the column number address contained in the first content addressable memory and the associated row number address to address the first read and write memory at a location near the right edge of a high contrast boundary;

searching the row number addresses sequentially of the second content addressable memory at a predetermined intensity level for a non-cleared content to locate a column number address;

using the column number address contained in the second content addressable memory and the associated row number address to address the second read and write memory at a location near the left edge of a high contrast boundary;

providing a search protocol for searching less than all of the video image and limited proximately to the iris of the human eye in the first and second read and write memories; and, using the search protocol to search the first and second read and write memories utilizing the row and column addresses of the predetermined intensity level whereby the iris of the human eye in the video image in the first and second read and write memories is searched by the search protocol.

7. A method of processing a video image including the iris of the human eye having first and second fields of image intensity data with known boundaries of high contrast according to claim 6:

wherein said video image includes a corneal reflection of a light source from the human eye, said video image of said corneal reflection having the highest level of intensity in said video image.

8. A method of processing a video image including the iris of the human eye having first and second fields of image intensity data with known boundaries of high contrast according to claim 1:

said image is a dark pupil image bounded by a bright image of the iris of the human eye, and said dark pupil is the lowest level of intensity in said video image.

9. A method of processing video images of the human eye having first video image with corneal reflection of a light source and second video image of an illuminated iris with a central dark aperture, both said video images having image intensity data with known boundaries of high contrast comprising the steps of:

providing first and second read and write memories each addressable by row number and column number addresses for storing image intensity data of the first video image with the corneal reflection and second video image of the illuminated iris at the row number and column number addresses;

providing first and second content addressable memories addressed by row number address and address related to image intensity for storing the column number address of the first and second video images at the row address and address related to image intensity;

initially clearing the first and second content addressable memories;

loading the first read and write memory by row number address and column number address to store image intensity data from the first video image with the corneal reflection;

loading the first content addressable memory by row number address and address related to image intensity to store column number address from the first video image with the corneal reflection;

searching the row number addresses sequentially of the first content addressable memory at a predetermined intensity level for a non-cleared content to locate a column number address of the corneal reflection;

using the column number address contained in the first content addressable memory and the row number address to address the first read and write memory at a location near the edge of a high contrast boundary of the corneal reflection;

loading the second read and write memory with row number address and column number address to store video intensity data from the second video image including the video image of the iris of the human eye;

clearing both content addressable memories;

loading the first content addressable memory by row number address and address related to image intensity to store column number address from the second read and write memory including the video image of the iris of the human eye;

loading the second content addressable memory by the row number address and related to image intensity address to store column number address from the second read and write memory including the video image of the iris of the human eye by reading the data from the memory in the reverse address order with respect to the first content addressable memory;

searching the row number addresses sequentially of the second content addressable memory at a predetermined intensity level for a non-cleared content to locate a column number address of the illuminated iris with a central dark aperture;

using the column number address contained in the first content addressable memory and the associated row number address to address the first read and write memory at a location near the right edge of a high contrast boundary;

searching the row number addresses sequentially of the second content addressable memory at a predetermined intensity level for a non-cleared content to locate a column number address;

using the column number address contained in the second content addressable memory and the associated row number address to address the second read and write memory at a location near the left edge of a high contrast boundary;

providing a search protocol for searching less than all of the video image in the first and second read and write memories; and, using the search protocol to search the first and second read and write memories utilizing the row and column addresses of the predetermined intensity level whereby less than all of the video image in the first and second read and write memories is searched by the search protocol.

10. A method of processing a video images of the human eye having first video image with corneal reflection of a light source and second video image of an illuminated iris with a central dark aperture, both said video images having image intensity data with known boundaries of high contrast according to claim 9:

comparing said centroid of said corneal reflection and said center of said pupil and outputting a difference signal related to the direction of gaze of said eye whereby said difference signal is a function of eye fixation.

11. A method of processing a video images of the human eye having first video image with corneal reflection of a light source and second video image of an illuminated iris with a central dark aperture, both said video images having image intensity data with known boundaries of high contrast according to claim 9:

locating a horizontal chord across said eye between the boundaries of said illuminated iris;

bisecting said horizontal chord; and taking a vertical dimension from said bisected chord to a boundary of said pupil.

12. A method of processing a video images of the human eye having first video image with corneal reflection of a light source and second video image of an illuminated iris with a central dark aperture, both said video images having image intensity data with known boundaries of high contrast according to claim 11:

locating ends of said chords by utilizing derivatives of the change of intensity of said image.

13. A method of processing a video images of the human eye having first video image with corneal reflection of a light source and second video image of an illuminated iris with a central dark aperture, both said video images having image intensity data with known boundaries of high contrast according to claim 12:

locating the ends of said chord by utilizing a first derivative of the change in intensity of said image to point to a zero crossing of said second derivative.

* * * * *